United States Patent [19]

Kuraishi et al.

[11] Patent Number: 5,071,466

[45] Date of Patent: Dec. 10, 1991

[54] METHOD OF DECREASING PHYSIOLOGICAL DROP FROM FRUIT TREES USING BRASSINOLIDE

[75] Inventors: Susumu Kuraishi, Hiroshima; Kazumi Sugiyama, Shimizu; Yoshikazu Yamaki, Ooiso; Yoshikazu Yamanaka, Hachioji; Kiyoshi Yokota, Morioka, all of Japan

[73] Assignee: Teijin Limited, Osaka, Japan

[21] Appl. No.: 574,192

[22] Filed: Aug. 28, 1990

Related U.S. Application Data

[63] Continuation-in-part of Ser. No. 333,585, Apr. 5, 1989, which is a continuation-in-part of Ser. No. 245,295, Sep. 16, 1988, abandoned.

[30] Foreign Application Priority Data

| Sep. 18, 1987 | [JP] | Japan | 62-232578 |
| Sep. 18, 1987 | [JP] | Japan | 62-232579 |
| Mar. 2, 1988 | [JP] | Japan | 63-47562 |
| Oct. 31, 1988 | [JP] | Japan | 63-272906 |
| Nov. 9, 1989 | [JP] | Japan | 63-281365 |

[51] Int. Cl.$^5$ ............................................. A01N 43/08
[52] U.S. Cl. ........................................................ 71/88
[58] Field of Search ............................. 71/88; 549/268

[56] References Cited

U.S. PATENT DOCUMENTS 3,038,794  6/1962  Geary et al. ............................ 71/2.5
4,346,226  8/1982  Thompson et al. .................. 549/268

OTHER PUBLICATIONS

Ref.A: Yopp et al., in Proc. 8th *Annual Meeting, Plant Growth Reg. Sac. of Am.* 1981, pp. 138–145. "Activity of Brassinosteroid . . .".
Ref.B: Meudt. *Ecology and Metabolism of Plant Lipids* Ch. 5, "Chem. and Bio. Aspects of Brasinolide", 1987, pp. 53–75.
Ref. C: Sugiyama et al., *Engei Gakkaishi* 58:2 (1989) "Effect of Brassinolide and Gibberellin . . .", p. 114.
*The Merck Index*, 10th ed., Merck & Co., Inc., p. 189, #1344, 1983.
Hers, Dieter. *Plant Physiology*, Springer-Verlag 1975, p. 204.
West, C. A. "New Growth Factors-Summary of Session" in *Plant Growth Substances* 1979, F. Skang, ed. Springer-Verlag, 1980. pp. 289–290.

Primary Examiner—Glennon H. Hollrah
Assistant Examiner—S. Mark Claroly
Attorney, Agent, or Firm—Wenderoth, Lind & Ponack

[57] ABSTRACT

A method of decreasing the physiological fruit drop from fruit trees, which comprises treating at least the overground portion of a growing citrus, peach, apple, pear or persimmon tree with a liquid agricultural composition comprising brassinolide in a concentration of above $1 \times 10^{-5}$ ppm to about 5 ppm.

6 Claims, No Drawings

METHOD OF DECREASING PHYSIOLOGICAL DROP FROM FRUIT TREES USING BRASSINOLIDE

This application is a continuation-in-part application of Ser. No. 07/333,585 filed on Apr. 5, 1989, which is continuation-in-part application of Ser. No. 07/245,297 filed on Sept. 16, 1988 now abandoned.

This invention relates to a method of decreasing or reducing physiological fruit drop which comprises treating a tree which bears or will bear the fruits with brassinolide.

Investigations on the growth regulation of plants, particularly the growth promotion of plants, have recently been undertaken extensively with respect to main cereals. Out of these investigations, plant hormones such as auxins, gibberellins, cytokinins, abscisic acid and ethylene have already emerged and come into practical acceptance, and many new plant hormones have further been proposed.

Brassinolide is one of those plant growth promoting substances which have recently been proposed. Brassinolide is a steroidal substance first discovered by Mitchell, Mandava et al. from the pollen of *Brassica napus* [see J. W. Mitchell, N. Mandava, J. P. Worley and J. P. Plimer: Nature, 225, 1065 (1970)). The work of Mitchell et al. led to the result that brassinolide had a very marked growing effect on second internodes of 7-day old bean seedings. Later, Mandava et al. determined brassinolide to have the following chemical structure [see Nature, 281, 216 (1979)].

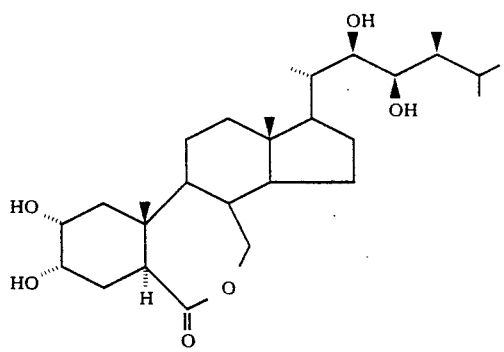

Brassinolide is a steroid having the complex structure given above, and various attempts have been made on its chemical synthesis. Furthermore, active research has been done on the development of its analogs and on their biological activities.

The effects of the biological activities of brassinolide on plants have been examined and reported. For example, brassinolide has a yield increasing effect on field crops and vegetables such as rice, corn, soybean, wheat, tomato and cucumber, a growth promoting effect on rice or corn, and an anti-stress effect on the aggravation of environments in which plants grow. They are described, for example, in SCIENCE, Vol. 212 (3) (April 1981) pp 33–34, Amer. J. Bot 68(4): pp 586–588, (1981).

Thus, research and development works on the brassinolide are made mainly with regard to principal field crops and vegetables, and their effects are yield increase, growth promotion and resistance to environmental stresses.

To the best of the present inventors' knowledge, however, no specific information has been published to date as to what effects brassinolide has on fruits when trees which bear or will bear the fruits are treated with brassinolide.

Fruit trees are cultivated in many countries of the world, and there are many varieties. In particular, citrus peach, apple and pear are grown abundantly. These fruits are nutritionally valuable, and are adapted for fresh fruit use or for processing.

Much efforts have therefore been made for breeding of new and more useful fruit cultivars.

On the other hand, fruit cultivating techniques have repeatedly been improved, and many new techniques for the yield increase of high quality fruits have been proposed. Environmental factors, particularly the influence of weather, are very difficut to control. Poor fructification and physiological fruit drop which are the disadvantages caused by the influence of environmental factors reduce the yield of fruits and degrade their quality.

It is an object of this invention to provide a method of decreasing physiological fruit drop of fruits from a citrus, peach, apple, pear or persimmon tree.

Another object of this invention is to provide a simple and economical method of decreasing physiological drop of the above fruits.

Still another object of this invention is to provide a method of obtaining many fruits or fruits of good quality by increasing fructification and decreasing physiological fruit drop.

Yet another object of this invention is to provide a method of increasing the fructification and the decreasing of physiological fruit drop of fruits, which occur as a result of aggravation of growing environments, particularly under the influence of bad weather.

Other objects of this invention will become apparent from the following description.

According to the investigations of the present inventors, the above objects of this invention are achieved by the following:

I. A method of decreasing physiological fruit drop of fruits from fruit trees, which comprises treating at least the overground portion of a growing citrus, peach, apple, pear or persimmon tree with a liquid agricultural composition comprising brassinolide as an active ingredient in a concentrations of about $1 \times 10^{-5}$ ppm to about 5 ppm.

According to this invention, a unique effect of brassinolide, which quite differs from that obtained heretofore on field crops or vegetables, can be obtained from its application to the fruit trees mentioned above. When the fruit trees are treated with brassinolide, the fructification ratio, the ratio of fruit set to the number of flowers, increases from that in the absence of the treatment, and the ratio of fruit drop (physiological fruit drop) to flower numbers is markedly reduced.

Thus, according to this invention, the ratio of ripe fruit set to flower numbers can be increased, and by the effect of increasing the fructification ratio and decreasing physiological fruit drop, the yield of fruits is increased, and also picking of fruits of unacceptable quality or selection of acceptable fruits can be artificially controlled. As a result, more fruits of good quality can be harvested.

Brassinolide used in this invention is known as 2α, 3α, 22R, 23R-tetrahydroxy-24S-methyl-B-homo-7-oxa-5α-colestan-6-one of the following chemical formula.

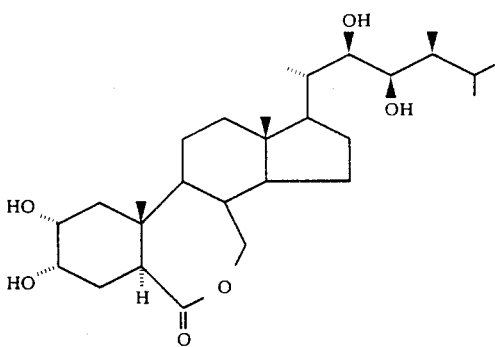

It has a melting point of 274° to 275° C. and is sparingly soluble in water.

Brassinolide is generally sparingly soluble in water, but exhibits activity even in very low concentrations. Usually, therefore, they may be used as a fine dispersion in water, or as an aqueous solution using a water-soluble organic solvent as a dissolving aid. A liquid composition comprising brassinolide and a method for its preparation will be described in detail hereinafter.

Fruits to which the invention is directed are citrus, peach, apple, pear and persimmon. Taxonomy of these fruits is shown below. In the present invention, the above "fruits" means those belonging to the species in the following list showing fruit tree names belonging to the respective species, and "spp" in the following list means species.

| Classification | Scientific nomenclature | English name |
|---|---|---|
| | A. (Citrus spp.) | |
| A-1 Limonellus (lime) | *Citrus aurantifolia* Swingle | lime |
| Citrophorum (citrons) | *Citrus jambhiri* Lush. | rough lemon |
| | *Citrus limon* Burm. f. | lemon |
| | *Citrus medica* L. | citron |
| | *Citrus medica* L. var. ethrog Engl. | ethrog citron |
| | *Citrus medica* L. var. sarcodactylis Swingle | fingered citron |
| | *Citrus pyriformis* Hassk. | ponderosa lemon |
| A-2 Cephalocitrus (pummelos) | *Citrus asahikan* hort. ex Tanaka | |
| | *Citrus glaberrima* hort. ex Tanaka | |
| | *Citrus grandis* Osbeck | shaddock, pummelo |
| | *Citrus grandis* Osbeck var. anseikan hort. ex Tanaka | |
| | *Citrus grandis* Osbeck var. banokan hort. ex Tanaka | |
| | *Citrus hassaku* hort. ex. Tanaka | |
| | *Citrus intermedia* hort. ex Tanaka | |
| | *Citrus paradisi* Macf. | grapefruit |
| | *Citrus pseudoparadisi* hort. ex Y. Tanaka | |
| A-3 Aurantium (oranges) | *Citrus aurantium* L. | sour orange, bitter orange, Seville orange |
| | *Citrus aurea* hort. ex Tanaka | |
| | *Citrus funadoko* hort. ex Y. Tanaka | |
| | *Citrus iyo* hort. ex Tanaka | |
| | *Citrus medioglobosa* hort. ex Tanaka | |
| | *Citrus natsudaidai* Hayata | |
| | *Citrus obovoidea* hort. ex Takahashi | |
| | *Citrus otachibana* hort. ex Y. Tanaka | |
| | *Citrus shunkokan* hort. ex Tanaka | |
| | *Citrus sinensis* Osbeck | sweet orange |
| | *Citrus sinensis* Osbeck var. brasiliensis Tanaka | navel orange |
| | *Citrus sulcata* hort. ex Takahashi | |
| | *Citrus tamurana* | |

-continued

| Classification | Scientific nomenclature | English name |
|---|---|---|
| | hort. ex Tanaka | |
| | Citrus tankan Hayata | tankan |
| | Citrus temple hort. ex Tanaka | temple |
| A-4 Osmocitrus | *Citrus hanaju* hort. ex Shirai | |
| | *Citrus junos* Sieb. ex Tanaka | |
| | *Citrus sphaerocarpa* hort. ex Tanaka | |
| | *Citrus sudachi* hort. ex Shirai | |
| | *Citrus yuko* hort. ex Tanaka | |
| A-5 Acrumen (tangerines, mandarins) | *Citrus clementina* hort. ex Tanaka | clementine mand |
| | *Citrus depressa* Hayata | |
| | *Citrus keraji* hort. ex Tanaka var. kabuchii | |
| | *Citrus kinokuni* hort. ex Tanaka | |
| | *Citrus leiocarpa* hort. ex Tanaka | |
| | *Citrus nobilis* Lour. var. Kunep Tanaka | |
| | *Citrus oto* hort. ex Y. Tanaka | |
| | *Citrus reshni* hort. ex Tanaka | reshni, cleopatra mandarin |
| | *Citrus reticulata* Blanco | ponkan mandarin ponkan |
| | *Citrus sunki* hort. ex Tanaka | |
| | *Citrus tachibana* Tanaka | |
| | *Citrus tangerina* hort. ex Tanaka | dancy tangerine |
| | *Citrus unshiu* Marc. | satsuma mandarin |
| | *Citrus unshiu* Marc. var. praecox tanaka | wase satsuma mandarin |
| | *Citrus yatsushiro* hort. ex Tanaka | |
| A-6 Pseudo-fortunella (Calamondin) | *Citrus madurensis* Lour. | calamondin |
| A-7 Fortunella (kumquats) | *Fortunella crassifolia* Swingle | meiwa kumquat, large round kumquat |
| | *Fortunella japonica* Swingle | round kumquat, marumi kumquat |
| | *Fortunella margarita* Swingle | oval kumquat, nagami kumquat |
| | *Fortunella obovata* Tanaka | changshou kumquat |
| A-8 Poncirus (trifoliate orange) | *Poncirus trifoliata* Raf. | trifoliate orange |
| B. Peach (Prunus spp.) | | |
| | *Prunus persica* Batsch var. nucipersica Schneid. | nectarine |
| | *Prunus persica* Batsch var. platycarpa L. H. Bailey | peento, flat peach |
| | *Prunus persica* Batsch var. vulgaris Maxim. | peach (common) |
| | *Prunus avium* L. | sweet cherry, mazzard cherry |
| | *Prunus besseyi* L.H. Bailey | western sand cherry |
| | *Prunus cerasus* L. | sour cherry, tart cherry, pie cherry |
| | *Prunus lannesiana* Wils. | |

-continued

| Classification | Scientific nomenclature | English name |
| --- | --- | --- |
| | Prunus mahaleb L. | mahaleb cherry, St. Lucie cherry |
| | Prunus pauciflora Bunge | Chinese cherry |
| | Prunus tomentosa Thunb. | Nanking cherry, Chinese bush cherry |
| | Prunus armeniaca L. | apricot |
| | Prunus mume Sieb. et Zucc. | mume, Japanese apricot |
| | Prunus cerasifera Ehrh. | Myrobalan plum, cherry plumm |
| | Prunus domestica L. | European plum, common plum |
| | Prunus insititia L. | bullace |
| | Prunus salicina Lindl. | Japanese plum |
| C. Apple (Malus spp.) | | |
| | Malus asiatica Nakai | |
| | Malus asiatica Nakai var. rinki Asami | |
| | Malus baccata Borkh. | red Siberian crab |
| | Malus cerasifera Spach | |
| | Malus halliana Koehne | Hall's crab apple |
| | Malus micromalus Mak. | |
| | Malus prunifolia Borkh. | yellow Siberian crab |
| | Malus prunifolia Borkh. var. ringo Asami | |
| | Malus pumila Mill. var. domestica Schneid. | apple |
| | Malus pumila Mill. var. paradisiaca Schneid. | paradise apple |
| | Malus sieboldii Rehd. | toringo crab |
| | Malus sieboldii Rehd. var. arborescens | |
| D. Pear (Pyrus spp.) | | |
| | Pyrus betulaefolia Bunge | |
| | Pyrus calleryana Decne. | callery pear |
| | Pyrus communis L. var. sativa DC. | pear, European pear |
| | Pyrus serotina Rehd. var. culta | Japanese pear, sand pear |
| | Pyrus ussuriensis Maxim. sinensis Kikuchi. | Chinese white pear |
| E. Persimmon (Diospyros spp.) | | |
| | Diospyros kaki Thunb. | Japanese persimmon, oriental persimmon, kaki |
| | Disopyros lotus L. | dateplum |

The fruit tree names listed above are typical ones belonging to the respective species, and varieties and hybrids of these fruit trees are of course included within the fruit trees to which the invention is directed.

The method of this invention has marked effects of increasing the fructification ratio and decreasing physiological fruit drop, and is therefore especially effective when it is anticipated that species have a problem of the decrease of the fructification ratio and the physiological fruit drop, or when the fruit trees are to be grown in an undesirable environment, or when varieties which are susceptible to these problems are to be grown. The present invention can especially increase the fructification ratio and decrease physiological fruit dropping on citrus trees. Among citrus fruits, varieties belonging to those called orange such as navel orange or sweet orange are liable to undergo these disadvantages depending upon environmental changes, and the method of this invention is effective for avoiding these disadvantages.

Liquid composition containing brassinolide and preparation thereof

As stated hereinabove, brassinolide is sparingly soluble in water, but exhibit activity even in very low concentrations. Usually, therefore, they may be used as a fine dispersion in water, or an aqueous solution using a water-soluble organic solvent as a dissolving aid.

The liquid composition containing the brassinolide may contain adjuvants generally used in agricultural chemicals, such as surface-active agents, emulsifiers or spreaders in order to increase the effect of the physiological activity of brassinolide and keep the liquid composition stable. This is usually preferred in performing the method of this invention.

The present invention provides the following two types of brassinolide containing liquid composition, composition A and composition B, which are equally used advantageously in decreasing physiologcal fruit dropping.

The concentration of brassinolide in any of these liquid compositions to be applied to the fruit trees may be very low. Advantageously, it may be generally about $1\times 10^{-5}$ ppm to 5 ppm, preferably $1\times 10^{-5}$ ppm to 3 ppm. The preferred range of the concentration of the brassinolide may vary depending upon the time of treatment, the method of treatment, the number of treatments, the type of the fruit trees, the purpose for which it is used, etc.

(A) A brassinolide-containing liquid composition (composition A)

Composition A is obtained by first dissolving brassinolide in a disolving aid, for example lower alcohols such as ethanol and propanol, lower ketones such as methyl ethyl ketone and methyl isobutyl ketone, and lower ethers such as ethyl ether, and then diluting the solution with water. Composition A may contain adjuvants generally used in agricultural chemicals, such as a surface-active agent, an emulsifier or a spreader, in order to increase the physiological activity of brassinolide and keep the composition stable.

Advantageously, composition A is composed of brassinolide in the aforesaid range, about 0.01 to about 2% by weight, preferably about 0.05 to about 1% by weight, of the dissolving aid, about 0.5 to about 20% by weight, preferably about 1 to about 15% by weight, in total of the adjuvants, and the remainder consisting substantially of water.

(B) A brassinolide-containing liquid composition (composition B)

Composition B is characterized by containing at least one solvent selected from the group consisting of amide-type polar solvents and dimethyl sulfoxide. Investigations of the present inventors have led to the result that composition B permits higher exhibition of the physiological activity of brassinolide than known brassinolide-containing compositions or composition A. Accordingly composition B can be advantageously applied not only for the purpose of decreasing physiological fruit drop, but also to the known use of brasinolide as plant hormones.

Composition B is a liquid agricultural composition consisitng essentially of an agriculturally effective amount of brassinolide and an organic mixture composed of (i) 50 to 98% preferably 50 to 95% by weight of a lower aliphatic alcohol, (ii) 1 to 25% preferably 1 to 20% by weight of a solvent selected from the group consisting of amide-type polar solvents and dimethyl sulfoxide, (iii) 1 to 25% preferably 1 to 15% by weight of a water-soluble polymer, based on the total weight of (i), (ii) and (iii) respectively and (iv) 0.002 to 2 parts by weight per part by weight of (i), (ii) and (iii) combined of a spreader, water being excluded in calculating the proportions.

In actual use for improving the physiological activities of plants, composition B is used as diluted with water. In this case, composition is diluted with about 100 to about 7,000 times, preferably about 200 to about 5,000 times, the weight of composition B, of water. Even when the composition is diluted to such an extent, it can be used without any trouble so long as the proportions of the ingredients calculated excluding water are within the aforesaid range.

The concentration of brassinolide in composition B in a form dilutd with water is desirably $1\times 10^{-5}$ ppm to 5 ppm.

The composition B brings about an excellent advantage in that the inclusion therein of (ii) at least one solvent selected from amide-type polar solvents and dimethylsulfoxide and (iii) the water-soluble polymer increases the activity of brassinolide from that in the absence of these materials (ii) and (iii), and the exhibition of its activity is stabilized.

The individual ingredients of composition B will be described below.

The lower aliphatic alcohol (i) may be, for example, methanol, ethanol, n-propanol, iso-propanol, n-butanol, iso-butanol or sec-butanol. Ethanol is preferred. The lower aliphatic alcohol is used in a concentration of 50 to 98% by weight, preferably 50 to 95% by weight, more preferably 60 to 90% by weight, based on composition B excluding the spreader (iv).

The solvent (ii) is selected from amide-type solvents and dimethylsulfoxide (DMSO). Examples of the amide-type solvents include dimethylformamide (DMF), N-methylpyrrolidone (NMP) and dimethylacetamide (DMAA). Among them DMF or NMP is especially preferred. The solvent (ii) is used in a concentration of 1 to 25% by weight, preferably 1 to 20% by weight more preferably 2 to 15% by weight, based on composition B excluding the spreader (iv).

Examples of the water-soluble polymer (iii) are polyalkylene glycols such as polyethylene glycol (PEG), polypropylene glycol and polybutylene glycol, polyvinyl pyrrolidone and polyvinyl alcohol. Polyethylene glycol (PEG) is especially preferred. Advantageously, the polyalkylene glycols have a molecular weight of 300 to 5,000, preferably 500 to 3,000. However, so long as they are soluble in lower aliphatic alcohols, their molecular weights are not particularly limited. The water-soluble polymer (iii) is used in a proportion of 1 to 25% by weight, preferably 1 to 15% by weight, more-preferably 2 to 10% by weight, based on composition B excluding the spreader (iv).

The spreader (iv) may be any spreaders which are normally used in agricultural chemical compositions such as a plant growth regulator, a herbicide, an insecticide, a fungicide and a mold-proofing agent. Specific examples of the spreader include polyoxyalkylene ethers such as polyoxyethylene dialkyl ethers, polyoxyethylene alkylaryl ethers and polyoxyethylene diaryl ethers; polyoxyalkylene diesters such as polyoxyethylene dialkyl esters, polyoxyethylene alkylaryl esters and polyoxyethylene diaryl esters; and sulfonate salts such as sodium dinaphthylmethanesulfonate, calcium ligninsulfonate and dialkyl sulfosuccinate. These spreaders are usually marketed for use in pesticide formulations, and can be used in this invention. They may also be used in combination. The proportion of the spreader (iv) is 0.002 to 2 parts by weight, preferably 0.003 to 1.0 parts by weight, especially preferably 0.03 to 0.5 parts by weight, per part by weight of (i), (ii) and (iii) combined.

Composition B may further contain a small proportion of a surface-active agent, an emulsifier, etc. which are usually employed in agricultural chemical compositions.

The composition B is prepared from brassinolide and the mixture of (i) to (iv). The amount of brassinolide may be very small because it exhibits its activity in small amounts. The proportion of brassinolide in composition B is very small. The concentration of brassinolide in composition B after dilution with water is within the range specified hereinabove, generally within the range of about $1 \times 10^{-5}$ ppm to 5 ppm. preferably $1 \times 10^{-5}$ ppm to 3 ppm.

Paste composition containing brassinolid, and preparation thereof

According to this invention, the objects of this invention can be also achieved by applying the agricutlural paste composition containing brassinolide to the aforesaid fruit trees.

A more preferred agricultural composition consists essentially of an agriculturally effective amount of brassinolide, (i) a lower aliphatic alcohol, (ii) a solvent selected from the group consisting of amide-type polar solvents and dimethyl sulfoxide, and (iii) a paste substrate.

Most·preferably, the agricultural past composition consists essentially of an agriculturally effective amount of brassinolide, (i) 5 to 30% by eight of a lower aliphatic alcohol, (ii) 0.01 to 1.0% by weight of a solvent selected from the group consisting of amide-type polar solvents and dimethyl sulfoxide, and (iii) 70 to 95% by weight of a paste substrate.

The concentration of brassinolide in the agricultural paste composition is generally $1 \times 10^{-6}$ ppm to 500 ppm, preferably $1 \times 10^{-3}$ ppm to 100 ppm, more preferably 1 to 50 ppm, especially preferably $1 \times 10^{-1}$ ppm to 30 ppm. The preferred range of the concentration of brassinolide in the agricultural paste composition depends upon the type of fruit to be treated, the time of treatment, the method of treatment, the number of treatments, etc.

In the agricultural paste composition comprising the components (I) and (II) particularly in the aforesaid proportions, the activity of brassinolide is increased and stabilized. Another advantage is that since it is in the form of a paste, its activity is stable and lasts for a long period of time.

The individual ingredients of the paste agricultural composition will be described below.

The lower aliphatic alcohol (i) may be, for example, methanol, ethanol, n-propanol, iso-propanol, n-butanol, iso-butanol or sec-butanol. Ethanol is preferred. The lower aliphatic alcohol is used in a concentration of 5 to 30% by weight, preferably 5 to 20% by weight, based on paste composition.

The solvent (ii) is selected from amide-type solvents and dimethlsulfoxide (DMSO). Examples of the amide-type solvents include dimethylformamide (DMF), N-methyl-pyrrolidone (NMP) and dimethylacetamide (DMAA). Among them DMF or NMP is especially preferred. The solvent (II) is used in a concentration of 0.01 to 1% by weight, preferably 0.05 to 0.8% by weight, based on composition B.

The paste substrate (iii) used in this invention is a material which retains its shape and is plastic at ordinary temperature. Preferably, it may generally be any of those paste substrates used in pastes containing various biologically active substances for application to humans, animals or plants. Examples of such paste substrates are fats, fatty oils, vaseline, lanolin, glycerol, higher alcohols and glycols. advantageously lanolin, vaseline and glycols, particularly dehydrated lanolin.

The agricultural paste composition may additionally contain other ingredients, for example plant hormones such as auxin and gibberellin, besides the ingredients (i) to (iii).

The agricultural paste composition of this invention can be prepared by mixing the above ingredients, preferably by first dissolving brassinolide in the solvent (ii), then adding the solution to the lower aliphatic alcohol, and mixing the solution with the paste substrate.

Method of decreasing physiological fruit dropping by the invention

The advantages of the treatment of the fruit trees with the liquid composition or the paste composition comprising brassinolide as an active ingredient in this invention are the increasing of the fructification ratio and the decrease of physiological fruit dropping. Hence, it is especially effective to treat the fruit trees during growth with the liquid agricultural composition or the agricultural paste composition of this invention when it is anticipated that the decrease of the fructification ratio and the physiological fruit drop will pose a problem, or when the fruit trees are to be grown in an undesirable environment, or when varieties which are susceptible to these problems are to be grown.

According to the method of this invention, the brassinolide-containing composition is applied to the overground portion of the growing fruit trees by such means as spraying or spreading. When the liquid composition is used, usually, it is desirable to apply the liquid composition to the leaves, stalks and inflorescence of the fruit trees. Generally, it is preferred to apply it to the entire fruit trees. The time of application depends upon the purpose of treatment. Generally, the bud-appearing stage, the flowering stage and the young fruit stage are preferred.

In a preferred embodiment of the method of this invention, the brassinolide-containing liquid composition is applied to the leaves, buds and inflorescence of the fruit trees by the whole tree spraying method. When it is to be applied during the flowering stage, it is more effective to spray it mainly on the inflorescenses.

By treating the fruit trees by the method of this invention in the bud-appearing stage, the flowering stage or a stage before it, the ratio of fructification is increased, and the physiological fruit drop can be decreased, as compared with the case of not performing the treatment. By treatment in the young fruit stage, the physiological fruit drop is decreased as compared with the case of not performing the treatment. In particular, when it is desired to decrease the physiological fruit drop, it is desirable to apply the brassinolide-containing composition in the early stage of the physiological fruit drop or before it. Even if it is before ripening of fruits, its effect of decreasing dropping in the ripe stage can be expected. Furthermore, by applying brassinolide during a period from three months to ten days before harvest, the weight of each fruit can be increased.

The treatment with brassinolide in accordance with the method of this invention is not limited to one time, and can be carried out several times. The concentration of brassinolide-containing composition does not have to be always constant, and may be varried depending upon the time of treatment.

The effective rate of application of the brassinolide-containing liquid composition to the orchard is about 10 liters to about 30,000 liters, preferably about 20 liters to about 10,000 liters, per hectare.

The composition B in accordance with this invention is very effective not only on the growth of fruit trees but also on the growth of other plants. The composition B of this invention exhibits a better effect when it is used to promote growth of field crops such as rice, corn, soybean and wheat, vegetables such as tomato and cucumber and ornamental plants, increase the yield of these crops and remove stresses on these plants.

To treat a fruit tree with the paste composition of this invnetion, it is preferred to coat it on the surface of the tree, its main body, its branches, its peduncle. Particularly, in the case of apple, coating of the paste composition o the peduncle between the fruit and the branch markedly reduces physiological fruit drop and much increases the yield of the apple fruit as compared with the case of not coating it. It has surprisingly been found that apple fruit harvested after the coating of the paste composition as above remain fresh for a long period of time. Accordingly, the present invention makes it possible not only to improve the yield of apple fruit but also to store apple fruit in a fresh state for a long period of time.

The following Examples illustrate the present invention more specifically.

In the liquid agricultural mixtures in the following examples, the following abbreviations are used.

BR: brassinolide
DMF: dimethylformamide
NMP: N-methylpyrrolidone
PEG 1000: polyethylene glycol having an average molecular weight of 1000
EtOH: ethanol
Neoesterin ®: speader comprising 20% of polyoxyethylene nonyl phenyl ether and 10% of polyoxyethylene fatty acid ester and polyoxyethylene resin acid ester (produced by Kumiai Chemical Co., Ltd.)
Tokubanno ®: speader containing 15% of polyoxyethylene alkylaryl ether and 7.5% of ligninsulfonate (made by Yamamoto Agricultural Chemicals Mfg., Co., Ltd.)
Banno ®: speader containing 20% of polyoxyethylene alkylphenyl ether and 12% of calcium lignin sulfonate (made by Yamamoto Agricultural Chemical Mtg., Co. Ltd.,)

EXAMPLE 1

[I] Preparation of mixtures

Mixtures in accordance of the following formulations were prepared.

| (1) Mixture A (blank) | |
|---|---|
| DMF | 50 g |
| PEG 1000 | 50 g |
| Neoesterin ® | 100 g |
| EtOH | 800 g |
| Total | 1000 g |
| (2) Mixture B | |
| BR | 25.1 mg |
| DMF | 250 g |
| PEG 1000 | 250 g |
| Neoesterin ® | 500 g |
| ETOH | 4000 g |

| -continued | |
|---|---|
| Total | 5000 g |
| (3) Mixture C | |
| BR | 25.1 mg |
| DMF | 25 g |
| PEG 1000 | 25 g |
| Neoesterin ® | 50 g |
| EtOH | 400 g |
| Total | 500 g |

Each of the above mixtures was used after dilution with 500 times its amount of water.

[II] Growth test (May to August, 1987)

Navel orange trees (Morita Navel; 10 years old) were used as test trees. Test areas each had one tree, and the test was carried out through 3 replicates. Test area 1 had a tree cultivated in a viny plastic house without warming. Test area 2 had a tree cultivated in an open field. Test area 3 had a tree cultivated in a vinyl-roofed area. In the prime stage of the flowering period, each of the mixtures A, B and C was diluted with water to 500-fold and sprayed on the entire trees in test areas 1, 2 and 3 by a hand sprayer on May 11. In particular, the mixture was sprayed mainly on the inflorescence of the trees.

On June 1 and 26, the number of fruits produced was examined, and on the basis of the number of flowers in the flowering period, the fructification ratio (%) was calculated. The results are shown in Table 1.

TABLE 1

| Test area | Spray liquid (BR concentration) | Fructification ratio (%) | |
|---|---|---|---|
| | | June 1 | June 26 |
| 1 | Mixture A (0) | 9.5 | 1.6 |
| | Mixture B (0.01 ppm) | 25.8 | 4.8 |
| | Mixture C (0.1 ppm) | 63.7 | 7.6 |
| 2 | Mixture A (0) | 9.4 | 1.8 |
| | Mixture B (0.01 ppm) | 15.9 | 3.2 |
| | Mixture C (0.1 ppm) | 14.8 | 14.8 |
| 3 | Mixture A (0) | 10.3 | 1.3 |
| | Mixture B (0.01 ppm) | 18.6 | 3.9 |
| | Mixture C (0.1 ppm) | 17.2 | 2.5 |
| Average | Mixture A (0) | 9.7 ± 0.4 | 1.5 ± 0.2 |
| | Mixture B (0.01 ppm) | 20.1 ± 4.2 | 4.0 ± 0.7 |
| | Mixture C (0.1 ppm) | 31.9 ± 22.5 | 8.3 ± 5.0 |

The results given in Table 1 demonstrate that the treatment with brassinolide decreased physiological fruit drop and increased the fructification ratio.

EXAMPLE 2

The same test areas and test trees as in Example 1 were separately provided, and the following test was carried out.

The trees were grown in a usual manner. On July 7 when fruits were produced after flowering, each of the mixtures A, B and C as in Example 1 was diluted with 500 times its amount of water and sprayed on the entire trees with a hand sprayer. The spray volume was 200 ml per tree.

The number of fruits produced was examined at the time of spraying (July 7) and on August 14. The fructification ratio on August 14 was calculated on the basis of the number of fruits produced at the time of spraying. The results are shown in Table 2.

TABLE 2

| Spray liquid (BR concentration) | Test area | Number of fruits produced (July 7) | Number of fruits produced (August 14) | Fructification ratio (%) | Average of fructification ratio (%) |
|---|---|---|---|---|---|
| Mixture A | 1 | 98 | 88 | 89.8 | 94.2 |
| (0) | 2 | 62 | 59 | 95.2 | |
| | 3 | 86 | 84 | 97.6 | |
| Mixture B | 1 | 72 | 72 | 100 | 99.4 |
| (0.01 ppm) | 2 | 58 | 58 | 100 | |
| | 3 | 112 | 110 | 98.2 | |
| Mixture C | 1 | 95 | 92 | 96.8 | 97.7 |
| (0.1 ppm) | 2 | 70 | 70 | 100 | |
| | 3 | 111 | 106 | 96.4 | |

It is seen from the results given in Table 2 that by spraying brassinolide after fructification, the physiological fruit drop after the spraying can be reduced.

EXAMPLE 3

Navel orange trees (variety Morita Navel; 10 years old) were used as test trees. Test areas each had one tree, and the test as carried out in 3 replicates. Test area 1 had a tree cultivated in a viny plasitc house without warming. Test area 2 had a tree cultivated in an open field. Test area 3 had a tree cultivated in vinyl roofed area.

On Oct. 5, 1987, each of the mixtures A and C was diluted to water to 500-fold and sprayed onto the entire trees with a hand sprayer.

On Dec. 22, 1987, the fruits were harvested, and weight and number of the fruits were examined. The results are shown in Table 3.

TABLE 3

| Spray liquid (BR concentration) | Test area | Yield (kg) | Number | Average weight per fruit | Brix | Acid (%) | Brix/acid ratio |
|---|---|---|---|---|---|---|---|
| Mixture A | 1 | 15.2 | 78 | 195 | 12.2 | 1.52 | 8.03 |
| (0) | 2 | 8.3 | 43 | 193 | 13.0 | 1.73 | 7.51 |
| | 3 | 8.3 | 36 | 231 | 11.9 | 1.61 | 7.39 |
| (Average) | | (10.6) | (52) | (206) | (12.4) | (1.62) | (7.64) |
| Mixture C | 1 | 18.4 | 95 | 194 | 12.6 | 1.48 | 8.51 |
| (0.1 ppm) | 2 | 8.2 | 31 | 265 | 11.6 | 1.41 | 8.23 |
| | 3 | 18.2 | 85 | 214 | 12.0 | 1.52 | 7.89 |
| (Average) | | (14.9) | (70) | (224) | (12.1) | (1.47) | (8.21) |

The results in Table 3 show that when the mixture containing 0.1 ppm of brassinolide (mixture C) was sprayed, the weight per fruit increased by about 10%, and the Brix/acid ratio became higher than in the blank (mixture A).

EXAMPLE 4

Mixtures having the following compositions were prepared.

| (1) Mixture D (blank) | |
|---|---|
| NMP | 15.0 g |
| EtOH | 285.0 g |
| total | 300.0 g |

| (2) Mixture E | |
|---|---|
| Neoesterin ® | 200 g |
| PEG 1000 | 100 g |
| EtOH | 150 g |
| | 450 g |

| (3) Mixture F | |
|---|---|
| BR | 20.0 mg |
| NMP | 20.0 g |
| EtOH | 380 g |
| | 400 g |

Ten milliliter of mixture F was taken, and 2.25 ml of mixture E was added to it. The mixture was diluted with 5 liters of water and used as spraying solution (mixture G) containing 0.1 ppm of BR.

One milliliter of mixture F was taken, and 2.25 ml of mixture E was added to it. The mixture was diluted with 5 liters of water, and used as a spraying solution (mixture H) containing 0.01 ppm of BR.

Mixture D (blank) was diluted with 500 times its amount of water, and used as a blank spryaing liquid (mixture J).

Growth test (May to September, 1987)

Trees of "Morita Navel" (11-year old) were used as test trees. One test area had one tree, and the test was performed in 6 replicates. The trees in the test areas were cultivated in an open field.

In the prime stage of flowering on May 9, each of mixtures G, H and J was sprayed onto the branch by using a hand sprayer at a rate of 100 ml per branch. Particularly, it was sprayed mainly on the inflorescence.

On May 26 and June 27, the number of fruits produced was examined in each of the test areas, and on the basis of the number of flowers in the prime stage of the flowering period, the fructification ratio (%) was calculated. The results are shown in Table 4.

TABLE 4

| Test area | Spray solution (concentration of BR) | Fructification ratio (%) May 26 | June 27 |
|---|---|---|---|
| 1 | Mixture G (0.1 ppm) | 62.0 | 8.3 |
| 2 | Mixture H (0.01 ppm) | 70.0 | 7.0 |
| 3 | Mixture J (blank) | 55.9 | 5.7 |
| 4 | Non-treated | 57.6 | 6.0 |

The fructification ratio in the blank and the non-treated area was relatively high because the flowering of the trees in that year was poor and the trees were well treated and were vigorous. The results given in Table 4 show that even under these conditions, the spraying of the brassinolide mixtures increased the furctification ratio.

EXAMPLE 5

[1] Preparation of mixture

A treating liquor or the following formulation was prepared.

| (1) Mixture A | |
|---|---|
| BR | 20 mg |

| -continued | |
|---|---|
| NMP | 20 g |
| EtOH | 380 g |
| Total | 400 g |
| (2) Mixture B | |
| PEG 1000 | 100 g |
| Neoesterin ® | 200 g |
| EtOH | 150 g |
| | 450 g |

To 10 ml of the mixture A was added 2.25 ml of the Mixture B. The mixture of A and B was diluted to 5 liters of water and used.

[II] Growth test was carried out using mature trees of persimmon ("hiratanenashi"—a seedless variety) cultivated in a field in an orchard experimental station in Japan. In each of treated areas, 50 fruits (flowers) were selected, and as a control, an area with 100 selected fruits (flowers) was used.

The treatment was carried out three days before flowering (test area A); three days after flowering (test area B); and 10 days after flowering (test area C). The flowing stage (the date on which the flowers were in full bloom) was May 26.

The treating liquid was sprayed on each treated area to such an extent that the buds and fruits were fully wetted. Four days later, the second spraying was carried out in each of the treated area.

The results were shown by the ratio of the fruits which dropped to the fruits (flowers) treated. Primary examination was made till three days after the flowering, and the examination was continued till 16-20 days after the flowering. The results are shown in Table 5.

TABLE 5

| (Days after flowering | Treated areas | | | |
|---|---|---|---|---|
| | A −3 | B +3 | C +10 | Control |
| Three days before flowering | treated | — | — | — |
| ~3 | 0 | treated | | 0 |
| 4–10 | 2 | 2 | treated | 1 |
| 11–15 | 4 | 8 | 14 | 29 |
| 16–20 | 6 | 16 | 16 | 11 |
| Cumulative fruit dropping ratio (%) | 12 | 26 | 30 | 41 |

It is seen from the results of Table 5 that by spraying brassinolide in the bud-appearing stage, the flowering stage and the young fruit stage, the ratio of physiological fruit dropping after spraying can evidently be reduced.

EXAMPLE 6

In this example, the effect of brassinolide on the fructification of peach was examined.

[I] Brassinolide-containiing liquid compositions used (1) Spray liquid having brassinolide concentration of 0

It was prepared by diluting the mixture A in Example 1 with 500 times its volume of water.

(2) Spray liquid having a brassinolide concentration of 0.01 ppm

It was prepared by diluting the mixture B in Example 1 with 500 times its volume of water.

(3) Spray liquid having brassinolide concentration of 0.05 ppm

It was prepared by diluting a mixture of equal amounts of the mixtures A and C in Example 1 with 500 times its volume of water.

[II] Growth test (April to May 1987)

Two peach trees (variety: "Chikuma") were used as test trees. On Apr. 17. 1987 (flowering of the trees began on April 18 and they were in full bloom on April three side branches were selected from each trees, and treated wholly with a spray of each of the spray liquids by using a hand sprayer. Immediately after the treatment, five branches bearing fruits were selected from each of the side branches, and the number of flowers was examined. On May 11, the number of fruits was examined. The results are shown in Table 6.

TABLE 6

| Spray liquid (BR concentration) | Test tree | Number of flowers at the time of treatment | Number of fruits produced | Fructification ratio (%) |
|---|---|---|---|---|
| 0.01 ppm | 1 | 19.6 | 11.4 | 63.2 |
| | 2 | 34.0 | 19.0 | 56.3 |
| | Average | 26.8 | 15.2 | 59.75 |
| 0.05 ppm | 1 | 27.8 | 23.2 | 83.1 |
| | 2 | 25.2 | 15.8 | 59.4 |
| | Average | 26.5 | 19.5 | 71.25 |
| 0 | 1 | 27.6 | 12.8 | 47.5 |
| | 2 | 23.4 | 11.4 | 50.1 |
| | Average | 25.5 | 12.1 | 48.8 |

It was confirmed from the results in Table 6 that by treatment with brassinolide just before flowering, the fructification ratio increased as compared with the absence of the treatment.

EXAMPLE 7

[I] Preparation of mixtures

Mixtures of the following formulations were prepared. Tokubanno ® was used after dilution with water to 10-fold.

| (1) Mixture A-1 (blank) | |
|---|---|
| EtOH | 5 ml |
| Water | 495 ml |
| Tokubanno ® | 1.5 ml |
| (2) Mixture A-2 (BR concentration 1 ppm) | |
| EtOH | 5 ml |
| Water | 495 ml |
| BR | 0.5 mg |
| Tokubanno ® | 1.5 ml |
| (3) Mixure A-3 (BR concentration $1 \times 10^{-2}$ ppm) | |
| Mixture A-2 | 5 ml |
| Water | 495 ml |
| Tokumanno ® | 1.5 ml |
| (4) Mixure A-4 (BR concentration $1 \times 10^{-4}$ ppm) | |
| Mixture A-3 | 5 ml |
| Water | 495 ml |
| Tokumanno ® | 1.5 ml |

(5) Mixture B-2 (BR concentration 1 ppm)

It was prepared by diluting 1 ml of a formulation consisting of 30 mg of BR, 3 g of DMF, 3 g of PEG 1000 and 48 g of EtOH with 499 ml of water, and adding 1.5 ml of Tokubanno ®.

(6) Mixture B-3 (BR concentration $1 \times 10^{-2}$ ppm)

It was prepared by diluting 1 ml of the formulation used in (5) above with 100 times its volume of a diluting liquid composed of 45 g of DMF, 45 g of PEG 1000 and 720 g of EtOH, further diluting 1 ml of the resulting dilution with 499 ml of water and adding 1.5 ml of Tokumanno ®.

(7) Mixture B-4 (BR concentration $1 \times 10^{-4}$ ppm)

It was prepared by diluting 0.01 ml of the formulation in (5) with 10,000 times its volume of the diluting liquid in (6), adding 499 ml of water to 1 ml of the resulting dilution, and adding 1.5 ml of Tokubanno ®.

[II] Growth test

Citrus unshiu Marc. (variety Fujinaka) trees (27 years old) were used as test trees, and the test was conducted in 1987.

On March 2, a chemical fertilizer comprising 10 kg each of N, P and K components was applied to the test trees at a rate of 62.5 g for each of P, N and K per tree. The trees were pruned on March 5.

A branch bearing about 10 flowers was used as one unit, and ten such branches were treated with each of the mixtures described above. On May 21 (in full bloom), each of the mixtures was sprayed onto the flowers and leaves with a hand sprayer.

On July 29 (69 days after the period of full bloom), the number of leaves and the number of fruits produced were examined in each of the treated area, and the number of leaves per fruit was calculated. The results are shown in Tables 7a and 7b.

TABLE 7a

| Spray liquid (BR concentration) | Treated area | Number of leaves | Number of fruits produced | Number of leaves/number of fruits produced |
|---|---|---|---|---|
| Mixture A-1 | 1 | 125 | 14 | 8.9 |
| (0) | 2 | 249 | 15 | 16.6 |
|  | 3 | 62 | 11 | 5.6 |
|  |  |  |  | (10.4) |
| Mixture A-3 | 1 | 131 | 16 | 8.2 |
| ($1 \times 10^{-2}$ ppm) | 2 | 107 | 15 | 7.1 |
|  | 3 | 150 | 14 | 10.7 |
|  |  |  |  | (8.7) |
| Mixture A-4 | 1 | 67 | 9 | 7.4 |
| ($1 \times 10^{-4}$ ppm) | 2 | 48 | 10 | 4.8 |
|  | 3 | 98 | 13 | 7.5 |
|  |  |  |  | (6.6) |

TABLE 7b

| Spray liquid (BR concentration) | Treated area | Number of leaves | Number of fruits produced | Number of leaves/number of fruits produced |
|---|---|---|---|---|
| Mixture B-2 | 1 | 139 | 18 | 7.7 |
| (1 ppm) | 2 | 85 | 13 | 6.5 |
|  | 3 | 103 | 26 | 4.0 |
|  |  |  |  | (6.1) |
| Mixture B-3 | 1 | 168 | 21 | 8 |
| ($1 \times 10^{-2}$ ppm) | 2 | 163 | 22 | 7.4 |
|  | 3 | 59 | 12 | 4.9 |
|  |  |  |  | (6.8) |
| Mixture B-4 | 1 | 38 | 14 | 2.7 |
| ($1 \times 10^{-4}$ ppm) | 2 | 56 | 11 | . |
|  | 3 | 80 | 13 | 6.. |
|  |  |  |  | (4.7) |

EXAMPLE 8

Preparation of mixtures

Mixtures of the following compositions were prepared.

| (1) Mixture A-1 (blank) | |
|---|---|
| Water | 495 ml |
| Banno ® | 1.50 ml |

(2) Mixtures B-1 (BR concentration 1 ppm)

Mixure B-1 was prepared by diluting 1 g of a composition composed of 30 mg of BR, 3 g of DMF, 3 g of PEG1000 and 54 g of EtOH with water to form 500 ml of a solution, and then adding 1.5 ml of Banno ® to the solution.

(3) Mixture B-2 (BR concentration $1 \times 10^{-2}$ ppm)

Mixture B-2 was prepared by diluting 1 g of the composition used in (2) above composed of 30 mg of BR, 3 g of DMF, 3 g of PEG1000 and 54 g of EtOH with a diluent solution composed of 45 g of DMF, 45 g of PEG1000 and 810 g of EtOH to 100 times. One gram of the resulting diluted solution was taken, and diluted to 500 ml with water, and adding 1.5 ml of Banno ®.

Growth test (1987)

Citrus unshiu Marc. variety ("Fujinaka") (27 year-old) trees were used as test trees, and the test was performed in 1987.

On March 2, a chemical fertilizer composed of 10 kg each of P, N and K per 10a was applied to test areas (the amount of each of K, N and K was 62.5 g per tree). On March 5, the trees were trimmed.

A branch bearing about 10 flowers in the test trees was designated as one unit, and three branch units were treated with each of the mixtures. When the trees were in full bloom, each of the mixtures was sprayed onto the flowers and leaves by using a hand sprayer.

On November 24 (harvesting time), the fruit juice ratio, the acid percent and the Brix/acid ratio in the treated area were examined, and the results are shown in Table 8.

TABLE 8

|  | Mixture | Fruit juice ratio (%) | Acid (%) | Brix/acid ratio |
|---|---|---|---|---|
| Control | Mixture A-1 | 43.4 | 1.06 | 9.70 |
|  | (Blank) | (100) | (100) | (100) |
| Example 1 | Mixture B-1 | 45.9 | 0.96 | 10.74 |
|  | (BR 1 ppm) | (106) | (91) | (111) |
| Example 2 | Mixture B-2 | 44.0 | 0.97 | 10.54 |
|  | (BR $1 \times 10^{-2}$ ppm) | (101) | (92) | (109) |

It is seen from the above table that mixtures B-1 and B2 which are the compositions of this invention are effective for increasing the fruit juice ratio and the Brix/acid ratio and decreasing the acid percent.

EXAMPLE 9

Preparation of a paste composition

A mixture of the following composition was prepared by using dehydrated lanolin (a product of Wako Pure Chemicals, Co., Ltd.) as a paste substrate

| BR | 5.4 mg |
| NMP | 0.5 g |
| EtOH | 51.5 g |
| dehydrated lanolin | 468 g |
| total | 520 g |

Growth test (August 1987 to April 1988)

The paste composition (BR 10 ppm) was coated on the peduncles of apples ("Fuji") on August 13 three months after the apple trees were in full bloom (May 10). August 13 was just before the stage where the growth of the fruits was most vigorous.

Investigation was conducted on Nov. 6, 1987, and on Apr. 30, 1988 after harvesting. The results are shown in Tables 9 and 10.

TABLE 9

(investigated on November 6, 1987)

| Treatment | investigated on August 18 | | investigated on November 6 | | | | | |
|---|---|---|---|---|---|---|---|---|
| | lateral diameter | longitudinal diameter | lateral diameter | longitudinal diameter | lateral/ longitudinal ratio | Brix | Hardness | Acid % |
| BR paste | 5.6 cm | 5.2 cm | 8.7 cm | 7.1 cm | 1.23 | 13.8 | 15.5 | 0.48 |
| Control | 5.5 | 5.2 | 7.9 | 6.9 | 1.14 | 14.6 | 15.1 | 0.42 |

Table 9 gives the average values for 10 fruits, and shows that the growth of the fruits was promoted mainly at the lateral diametr, and the ratio of the lateral diameter to the longitudinal diameter apparently became high.

TABLE 10

(freshness investigation on April 30, 1987)

| Treatment | Brix (%) | Hardness | Acid % |
|---|---|---|---|
| BR paste | 13.4 13.8 18.8 | 13.4 14.0 13.7 | 0.32 |
| control | 13.6 13.5 14.0 | 12.8 12.5 12.5 | 0.28 |

The Brix and hardness were measured on three individuals, and the acid percent was measured on a juice prepared from three individuals. The data given in Table 10 demonstrate that the apple fruits had a high hardness and their freshness was retained for a long period of time.

EXAMPLE 10

A paste composition containing 10 ppm of brassinolide and prepared as in Example 9 was used, and a test was carried out on the growth of apple. The test apple variety was "Tsugaru", and test apple trees were treated on July 22, 1988 by coating the paste composition on the peduncle. The apple fruits were harvested on September 21.

In the treated area, thirty fruits were treated, and in the non-treated area, twenty fruits were examined.

The results are shown in Table 11.

TABLE 11

(dropping of fruits before harvest)

| | Total fruits number | Number of fruits which dropped before harvest | Number of fruits harvested | Fruit dropping ratio (%) |
|---|---|---|---|---|
| paste composition is used | 30 | 1 | 29 | 3.3 |
| non-treated | 20 | 8 | 12 | 40.0 |

TABLE 11-continued (dropping of fruits before harvest)

| | Total fruits number | Number of fruits which dropped before harvest | Number of fruits harvested | Fruit dropping ratio (%) |
|---|---|---|---|---|
| treated | | | | |

Table 11 shows that the treatment with brassinolide clearly decreased physiological fruit drop.

EXAMPLE 11

Apple trees ("Tsugaru") were used as test trees. One main branch of each test trees was selected for investigation and investigation was carried out in three replicates.

Each of the mixture A, B and C in Example 1 was diluted with 500 times its amount of water and was sprayed on the main branches throughly on July 26, August 2 and Aug. 9, 1989.

The fruit dropping ratio were investigated on September 13 and Sept. 20, 1989. The results were shown in Table 12.

TABLE 12

| | Fruit Dropping Ratio (%) Investigated on | |
|---|---|---|
| | September 13 | September 20 |
| Mixture A (0) | 3.0 | 10.0 |
| Mixture B (0.01 ppm) | 1.0 | 6.0 |
| Mixture C (0.1 ppm) | 0 | 2.0 |

We claim:

1. A method of decreasing physiological drop of fruits from fruit trees, which comprises treating at least the branches and/or foliage of a growing citrus, peach, apple, pear or persimmon tree with a liquid agricultural composition comprising brassinolide in a concentration of about $1 \times 10^{-5}$ ppm to about 5 ppm.

2. The method of claim 1 in which the liquid agricultural composition is sprayed at least onto the inflorescence of the fruit tree.

3. The method of claim 1 in which the liquid agricultural composition is sprayed entirely onto the branches and/or foliage of the tree at least once in a period from the bud appearing stage to the harvesting stage.

4. The method of claim 1 in which the tree is treated with the liquid agricultural composition at least in the bud appearing stage, the flowering stage and/or the young fruit stage.

5. The method of claim 1 in which the liquid agricultural composition is sprayed onto at least the inflorescence of the tree at least in the flowering stage.

6. The method of claim 1 in which the liquid agricultural composition is applied at a rate of about 10 liters to about 30,000 liters in total per hectare once or a plurality of times.

* * * * *